United States Patent [19]

Greenwood

[11] 4,104,577

[45] Aug. 1, 1978

[54] MAGNETIC RESONANCE APPARATUS

[75] Inventor: Ivan Anderson Greenwood, Stamford, Conn.

[73] Assignee: The Singer Company, Little Falls, N.J.

[21] Appl. No.: 765,135

[22] Filed: Feb. 2, 1977

[51] Int. Cl.² .......................................... G01R 33/08
[52] U.S. Cl. .............. 324/0.5 F; 324/0.5 R; 324/0.5 AH
[58] Field of Search .............. 356/75, 246; 324/0.5 R, 324/0.5 F, 0.5 MA, 0.5 A, 0.5 AH, 0.5 E

[56] References Cited

U.S. PATENT DOCUMENTS

| | | | |
|---|---|---|---|
| 3,227,944 | 1/1966 | Hasty | 324/0.5 R |
| 3,396,349 | 8/1968 | Rider | 324/0.5 AH |
| 3,516,744 | 6/1970 | Hinman et al. | 356/75 |
| 3,534,251 | 10/1970 | Richards | 324/0.5 AH |
| 3,750,008 | 7/1973 | Asano | 324/0.5 F |

*Primary Examiner*—M. Tokar
*Attorney, Agent, or Firm*—Thomas W. Kennedy

[57] ABSTRACT

Magnetic resonance apparatus having an alignment axis which is located in and oriented parallel to a unidirectional field when the apparatus is in operation. The apparatus includes an absorption cell intersected by the alignment axis having a plurality of surface elements surrounding a hollow cell interior in which a magnetic resonance medium is located. The improvement of the invention is the absorption cell having normals to its surface elements which simultaneously form angles of around 55° with lines parallel to the alignment axis.

18 Claims, 5 Drawing Figures

MAGNETIC RESONANCE APPARATUS

BACKGROUND OF THE INVENTION

1. Field of the Invention

The invention herein described was made in the course of or under a contract, or subcontract thereunder, with the Department of the Air Force.

This invention relates to magnetic resonance apparatus in general and in particular to an improved apparatus having an alignment axis which is located in and oriented parallel to a unidirectional magnetic field when the apparatus is in operation and an absorption cell intersected by the alignment axis having a plurality of surface elements surrounding a hollow interior in which a magnetic resonance medium is located.

2. Description of the Prior Art

Current magnetic resonance apparatus, such as gyroscopes and magnetometers, use optical pumping beams to increase signal strength by preferentially increasing the proportion of the sample material, or magnetic resonance medium, in a given spin state. The excess population, however, relaxes back into its prior state by means of one or more processes, each characterized by a relaxation time.

An increased relaxation time results in a stronger signal and better signal stability. In current apparatus, however, the relaxation time can be undesirably short where relaxation by means of a quadrupole interaction is possible. For example, in nuclear magnetic resonance apparatus, the relaxation time for nuclei with spin greater than one-half is affected whenever these nuclei can relax by means of quadrupole interactions. The rate of these quadrupole interactions depends in part upon the geometry of the cell containing the magnetic resonance medium. A further disadvantage of current apparatus is a broadening of the resonance lines caused by the quadrupole interactions.

SUMMARY OF THE INVENTION

It is therefore an object of the invention to provide a magnetic resonance apparatus which has improved signal strength and signal stability, increased relaxation time of the magnetic resonance media and less quadrupole induced broadening of resonance lines.

This and other objects of the invention are achieved in a magnetic resonance apparatus having an alignment axis which is located in and oriented parallel to a unidirectional magnetic field when the apparatus is in operation and an absorption cell intersected by the alignment axis. The absorption cell has a plurality of surface elements surrounding a hollow cell interior in which a magnetic resonance medium is located. The normals to the cell's surface elements simultaneously form angles of around 55° with lines parallel to the alignment axis.

The present invention also provides a method for generating an improved magnetic resonance signal in a magnetic resonance apparatus having an alignment axis which is located in and oriented parallel to a unidirectional magnetic field when the apparatus is in operation. An absorption cell having a plurality of surface elements surrounding a hollow cell interior in which a magnetic resonance medium is located is shaped such that the normals of the surface elements simultaneously form angles of around 55° with lines parallel to the alignment axis. At least one optical beam is passed at least into the cell interior.

These and other features of the invention will be described in greater detail in the following detailed description.

DETAILED DESCRIPTION

Figure 1:
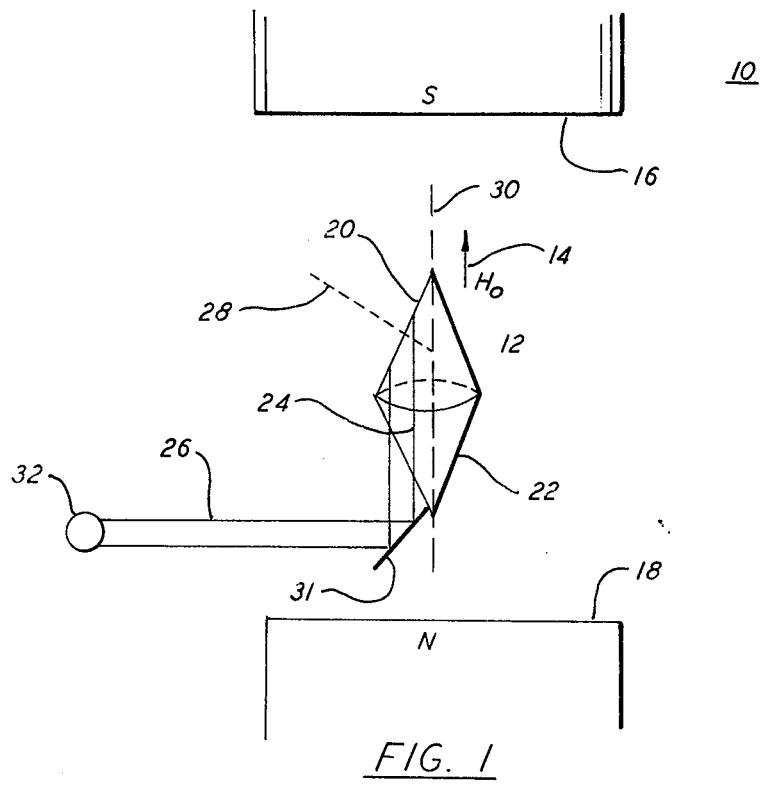
FIG. 1 is a schematic illustration of a portion of an improved magnetic resonance apparatus constructed in accordance with the present invention.

Referring now to the drawings, and in particular to FIG. 1, there is shown a schematic illustration of a portion of an improved magnetic resonance apparatus 10 including an absorption cell 12. The apparatus 10 may be, for instance, a gyroscope or a magnetometer.

Apparatus 10 includes alignment axis 30 which is in and parallel to unidirectional magnetic field $H_o$, the direction of which is indicated by the arrow 14. The field generating means are shown as magnet faces 16 and 18. Pole 16 has south polarity and pole 18 has north polarity. Magnetic field $H_o$ fills the space in and surrounding cell 12. In the case of a magnetometer, the unidirectional magnetic field is generated primarily by the earth or some other source and not by any means integral to the apparatus itself.

Cell 12 is composed of transparent non-magnetic surface elements 20 and 22 which surround the hollow cell interior 24 in which is located the magnetic resonance medium. In nuclear magnetic resonance gyroscopes, cell interior 24 can contain two odd isotopes of mercury, i.e., $^{199}Hg$ and $^{201}Hg$. A typical material of construction is fused silica.

The field $H_o$ separates the energies of the spin states of the magnetic resonance medium. For example, $^{199}Hg$ has a nuclear spin of one-half and therefore has two spin states, the energies of which are separated by field $H_o$. $^{201}Hg$, however, has a nuclear spin of three-halves and therefore four spin states whose energies are separated by the field.

Optical pumping beam 26 acts in the known manner on the magnetic resonance medium to preferentially increase the proportion of the medium in a given spin state or states. The result of optical pumping is an enhancement of the magnetic moment of the medium. In the case of $^{199}Hg$ and $^{201}Hg$ the magnetic moment of each isotope is enhanced.

The excess population in the various spin states of the magnetic resonance medium resulting from the optical pumping relaxes back into its prior state by means of one or more processes, each characterized by a relaxation time. Typically, the relaxation time of $^{199}Hg$ is greater than that of $^{201}Hg$ because $^{201}Hg$, having a nuclear spin of three-halves, can relax by means of an electric quadrupole interaction, whereas $^{199}Hg$ cannot. Even in the absence of optical pumping, the quadrupole interaction is undesirable since it results in a broadening of the resonance lines.

To repress the quadrupole interaction in accordance with this invention, the absorption cell containing the magnetic resonance medium is oriented such that the normals to the cell's surface elements make angles of around 55° with lines parallel to alignment axis 30. One possible shape of such a cell is shown in FIG. 1.

Cell 12 is in the shape of a bicone whose nominal half cone angle, 35.26°, is chosen so that normal 28 to surface element 20 and the normal not shown to surface element 22 make angles of around 55° with alignment axis 30. The angles ± 55° approximate the roots of $P_2(COS\theta) = 0$, where $P_2$ is the Legendre polynomial of the first kind of order two.

It is preferable that pumping beam 26 be circularly polarized to most efficiently perform its function. A strongly tilted surface, such as that of surface element 22 will, as is known, change the polarization of an incident pumping beam. To compensate for this effect, beam 26 is elliptically polarized in beam source 32 so that as beam 26 enters the cell the above-mentioned effect changes the polarization to circular. Beam source 32 typically could consist of a light source, a linear polarizer and a quarter-wave plate oriented at such an angle to the plane of the linearly polarized light so as to generate the proper elliptical polarization. Beam 26 is emitted from beam source 32, strikes mirror 31 and is reflected so that it enters cell 12 parallel to alignment axis 30.

Figure 2:
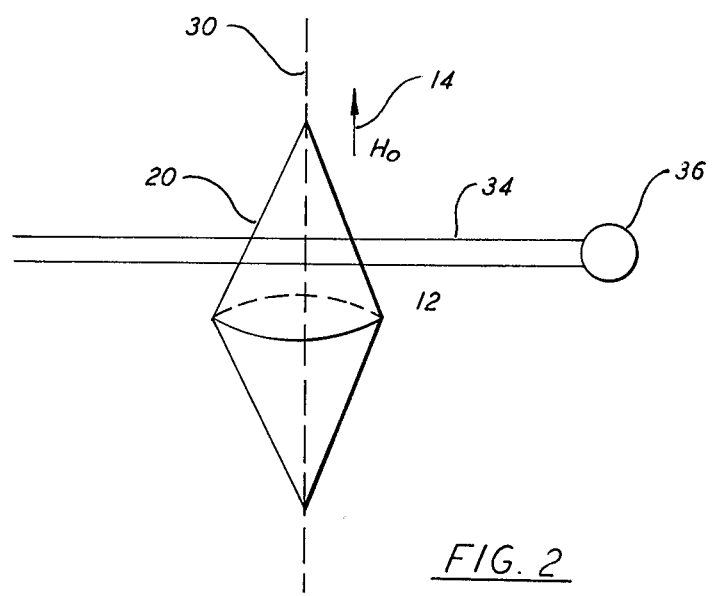
FIG. 2 is a schematic illustration of a portion of FIG. 1 and an optical readout beam.

Referring now to FIG. 2, there is shown cell 12 being intersected by an optical readout beam 34 originating from beam source 36. As is known, a separate readout beam as shown in FIG. 2 is not always required: the readout beam and the pumping beam can be the same beam. Or in some cases, no pumping beam is used at all. If a separate readout beam is used, it is common to use Faraday readout to analyze the readout beam. In that case readout beam 34 must be linearly polarized and the plane of polarization is preferably at an angle of about 55° with respect to field direction 14 or else the readout beam itself can induce electric quadrupole interactions. Because of the effect of the tilted surface of surface element 20, however, the polarization angle with respect to field direction 14 of the readout beam must be offset. Then by crossing surface element 20, the polarization angle is converted to the proper 55° angle.

Figure 3:
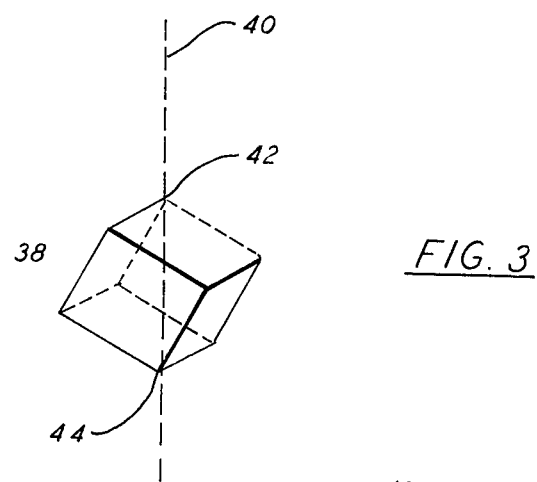
FIG. 3 is a schematic illustration of a cell in the shape of a cube as used in the present invention.

FIG. 3 depicts another shape for an improved cell according to the invention. Cube-shaped cell 38 must be oriented such that the alignment axis 40 passes through corners 42 and 44. Of course, any other shape which, like the cube, has each surface element parallel to a face of a cube also has the proper shape to result in an increased relaxation time. That is, both a cell in the shape of a rectangular solid and a cubic cell would repress the quadrupole interaction if used in accordance with the present invention.

Figure 4:
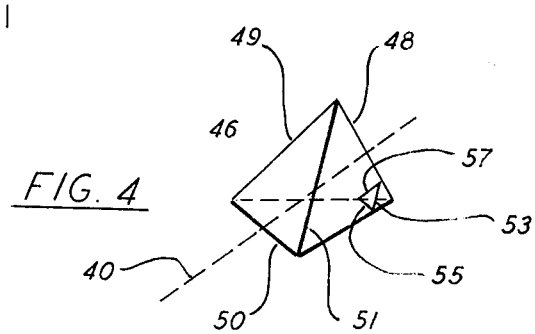
FIG. 4 is a schematic illustration of a cell in the shape of a regular tetrahedron as used in the present invention.

FIG. 4 represents a regular tetrahedral cell 46 according to the invention. Cell 46 must be oriented such that alignment axis 40 is perpendicular to two opposed edges 48 and 50.

A cell in the shape of cell 46 but with one corner cut off parallel to the face of cell 46 defined by edges 49, 50 and 51 would still have the proper shape to repress the quadrupole interaction. Such a cut is indicated by finely dotted lines 53, 55 and 57. The common feature of cell 46 and cells such as that made by the cut represented by lines 53, 55 and 57 is that each surface is parallel to a face of a regular octahedron, or equivalently, to a face of a positive or negative regular tetrahedron. All such geometries are examples of the class of shapes which would accomplish the objectives of this invention.

Figure 5:
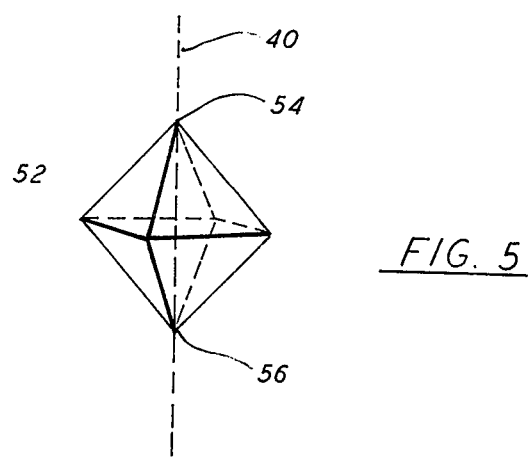
FIG. 5 is a schematic illustration of a cell in the shape of a regular octahedron as used in the present invention.

FIG. 5 depicts a regular octahedral cell 52 according to the invention. Cell 52 must be oriented such that alignment axis 40 passes through corners 54 and 56. As in the case of the cubic and regular tetrahedral cells, not only a regular octahedral-shaped cell but also any other cell whose surface elements are parallel to faces of octahedra so-oriented could be used in this invention.

It should be noted that not only the relatively simple cell shapes listed above but also any mixture of these shapes in a single cell would also have the proper geometry and therefore would be useable in this invention.

Cells 38, 46 and 52 have an advantage over cell 12 in that they have relatively large, flat surfaces which facilitate the introduction of pumping beam 26 and readout beam 34 into the cell.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are, accordingly, to be regarded in an illustrative rather than in a restrictive sense.

What is claimed is:

1. In a magnetic resonance apparatus having an alignment axis which is located in and oriented parallel to a unidirectional magnetic field when the apparatus is in operation and an absorption cell intersected by the alignment axis having a plurality of surface elements, each of said plurality of surface elements having a normal, surrounding a hollow cell interior in which a magnetic resonance medium is located, the improvement comprising: the absorption cell having surface elements the normals of which simultaneously form angles of around 55° with lines parallel to the alignment axis.

2. The invention as recited in claim 1 further comprising at least one polarized optical pumping beam which pumping beam passes into the cell interior, the polarization of that part of the beam lying in the cell interior being circular.

3. The invention as recited in claim 1 further comprising a linearly polarized optical readout beam passing through the cell interior, the direction of polarization of that part of the readout beam lying in the cell interior forming an angle of around 55° with the alignment axis.

4. The invention as recited in claim 1 further comprising means for generating a unidirectional magnetic field which field intersects the absorption cell and with respect to which the alignment axis can be oriented.

5. The apparatus as recited in claim 1 wherein the magnetic resonance medium is a nuclear magnetic resonance medium in vapor form.

6. The apparatus as recited in claim 1 wherein the surface elements form a bicone.

7. The apparatus as recited in claim 1 wherein each surface element is parallel to a face of a cube.

8. The apparatus as recited in claim 1 wherein each surface element is parallel to a face of a regular tetrahedron.

9. The apparatus as recited in claim 1 wherein each surface element is parallel to a face of a regular octahedron.

10. A method for generating an improved magnetic resonance signal in a magnetic resonance apparatus having an alignment axis which is located in and oriented parallel to a unidirectional magnetic field when the apparatus is in operation comprising:

(a) orienting an absorption cell having a plurality of surface elements, each of said plurality of surface elements having a normal, surrounding a hollow cell interior in which a magnetic resonance medium is located such that the normals of the surface elements simultaneously form angles of around 55° with lines parallel to the alignment axis and the alignment axis intersects the cell; and (b) passing at least one optical beam at least into the cell interior.

11. The method as recited in claim 10 wherein the optical beam is a polarized beam, the polarization of that part of the beam lying in the cell interior being circular.

12. The method as recited in claim 10 wherein the optical beam is a readout beam, and the optical beam passes through the cell interior.

13. The method as recited in claim 12 wherein the readout beam is linearly polarized, the direction of polarization of that part of the readout beam lying in the cell interior forming an angle of around 55° with the alignment axis and further comprising passing a polarized optical pumping beam into the cell interior, the polarization of that part of the pumping beam lying in the cell interior being circular.

14. The method as recited in claim 10 wherein the optical beam is both a pumping beam and a readout beam, and the optical beam passes through the cell interior.

15. The method as recited in claim 10 wherein the surface elements form a bicone.

16. The method as recited in claim 10 wherein each surface element is parallel to a face of a cube.

17. The method as recited in claim 10 wherein each surface element is parallel to a face of a regular tetrahedron.

18. The method as recited in claim 10 wherein each surface element is parallel to a face of a regular octahedron.

* * * * *